(12) United States Patent
Louie

(10) Patent No.: US 8,304,523 B1
(45) Date of Patent: Nov. 6, 2012

(54) NANOWIRE MANUFACTURE AND APPROACHES THEREFOR

(75) Inventor: Ryan K. Louie, San Francisco, CA (US)

(73) Assignee: The Board of Trustees of the Leland Stanford Junior Universtiy, Palo Alto, CA (US)

( * ) Notice: Subject to any disclaimer, the term of this patent is extended or adjusted under 35 U.S.C. 154(b) by 1308 days.

(21) Appl. No.: 11/402,647

(22) Filed: Apr. 12, 2006

Related U.S. Application Data

(60) Provisional application No. 60/670,554, filed on Apr. 12, 2005.

(51) Int. Cl.
*A23J 1/00* (2006.01)
(52) U.S. Cl. ........................................ 530/412
(58) Field of Classification Search ............... None
See application file for complete search history.

(56) References Cited

U.S. PATENT DOCUMENTS

| | | | |
|---|---|---|---|
| 5,492,696 | A | 2/1996 | Price et al. |
| 5,651,976 | A | 7/1997 | Price et al. |
| 5,705,191 | A | 1/1998 | Price et al. |
| 5,916,642 | A | 6/1999 | Chang |
| 6,280,759 | B1 | 8/2001 | Price et al. |
| 6,465,132 | B1 | 10/2002 | Jin |
| 6,762,331 | B2 | 7/2004 | Hong et al. |
| 2004/0210289 | A1* | 10/2004 | Wang et al. ............ 607/116 |

OTHER PUBLICATIONS

Behrens et al. Chem. Mater. 2004, vol. 16, pp. 3085-3090; May 2004.*
Jia et al. Biomed Microdevices. vol. 6, No. (1), pp. 67-74, Mar. 2004.*
Ross et al. Biophysical Journal, vol. 84, No. 6, pp. 3959-3967, Jun. 2003.*
Reches et al. Science, vol. 300, pp. 625-627, Apr. 2003.*
Fritzsche et al. (Appl. Phys. Lett. 75, 2854, 1999).*
Scheibel, T. et al. *Proc Natl Acad Sci USA* 100, 4527-4532 (2003).
Reches, M. & Gazit, E. *Science* 300, 625-627 (2003).
McMillan, R.A. et al. *Nat Mater.* 1, 247-252 (2002).
Desai A. & Mitchison T.J. *Annu Rev Cell Dev Biol.* 13, 83-117 (1997).
Nogales, E. et al. *Cell* 96, 79-88 (1999).
Burton, P.R. *J Cell Biol.* 99, 520-8 (1984).
Odde D. *Eur Biophys J.* 27, 514-520 (1998).
Diaz, J.F. et al. *J Biol Chem.* 273, 33803-33810 (1998).
Ross, J.L. & Fygenson, D.K. *Biophys J.* 84, 3959-3967 (2003).

* cited by examiner

*Primary Examiner* — Michael Burkhart
(74) *Attorney, Agent, or Firm* — Crawford Maunu PLLC

(57) ABSTRACT

Nanowires are constructed using a variety of methods. Using one such method, a nanowire material is introduced to a microtubule lumen as a solution. The nanowire material is solidified to form a nanowire substantially within the microtubule lumen.

26 Claims, 2 Drawing Sheets

NANOWIRE MANUFACTURE AND APPROACHES THEREFOR

RELATED PATENT DOCUMENTS

This patent document claims the benefit, under 35 U.S.C. §119(e), of U.S. Provisional Patent Application No. 60/670,554, entitled "Metallic Nanowires Cast from Microtubule Lumens" as was filed on Apr. 12, 2005.

FEDERALLY-SPONSORED RESEARCH AND DEVELOPMENT

This invention was made with Government Support under contracts GM007365 and DK056339 awarded by the National Institutes of Health (NIH). The U.S. Government has certain rights in this invention.

FIELD OF THE INVENTION

The present invention relates generally to nanowires, and more particularly to the use of microtubule structures for creating nanowires.

BACKGROUND

There has been an increasing desire to produce smaller and smaller devices in the fields of, among other things, chemistry, biology, electronics and mechanical devices. When the devices approach the size of biological cells, the technology is often referred to as nano-scaled or as nanotechnology. The field of nanotechnology has already proven useful for numerous applications; however, many issues still exist in the development and implementation of nanotechnology.

Some applications of nanotechnology require characteristics of nano-scale structures called nanowires. A nanowire is a wire of dimensions of the order of a nanometer ($10^{-9}$ meters). Many types of nanowires exist, including metallic, semiconducting, and insulating. They have shown promise in mechanical, chemical, and electrical applications.

There has been growing interest in the formation of new molecular components built with a "bottoms-up" approach: small molecularly-precise parts coming together to become larger ordered complexes, all orchestrated by a series of controlled assembly events. Proteins have proven to be useful building templates for assembling metallic material, with such biologically-inspired examples as nanowires made from amyloidal fibers and peptide nanotubes, and nanoparticle arrays made from heat shock proteins. For additional information regarding device-implementation and manufacturing approaches for nanotube and nanowire structures, reference may be made, for example, to U.S. Pat. No. 5,916,642, U.S. Pat. No. 6,465,132 and U.S. Pat. No. 6,762,331; each of these references is fully incorporated herein by reference.

While nanotechnology has progressed, many challenges remain. For example, applications involving applying metal to the exterior of a protein polymer result in the metal encasing the protein polymer along the length of the polymer, and thus, the protein polymer loses its ability to interact with other molecules. Moreover, it can be difficult to control the thickness of the metal applied to the polymer.

Additionally, producing synthetic organic nanotubes and creating the nanowires inside the nanotubes requires the nanotubes to be synthesized using laboratory controlled organic chemistry, often increasing the production costs and creating problems with producing large quantities of the nanotubes. It is also difficult to control the size of the nanotubes resulting in unwanted variations in the nanowires created.

For these and other reasons, the manufacture and implementation of nanowires has been challenging.

SUMMARY

The claimed invention is directed to overcoming the above-mentioned challenges and others related to nanowires and nanowire fabrication. The present invention is exemplified in a number of implementations and applications, some of which are summarized below.

Various example embodiments of the present invention are directed to methods for constructing nanowires. Using one such method, a nanowire material is introduced to a microtubule as a solution. The nanowire material is solidified to form a nanowire shaped by the microtubule.

In another embodiment, tubulin is aliquoted and stored in G-PEM buffer plus glycerol. Tubulin is polymerized in the presence of a paclitaxel solution to produce a microtubule lumen. The microtubule lumen is incubated in a silver nitrate solution. The silver nitrate is reduced to a silver solid in citric acid, resulting in a substantial portion of the silver solid being located within the interior of the microtubule lumen.

In yet another embodiment, a nanowire is constructed by casting a material using the interior of a microtubule lumen.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which various aspects are described in the Detailed Description below, where.

Figure 1:
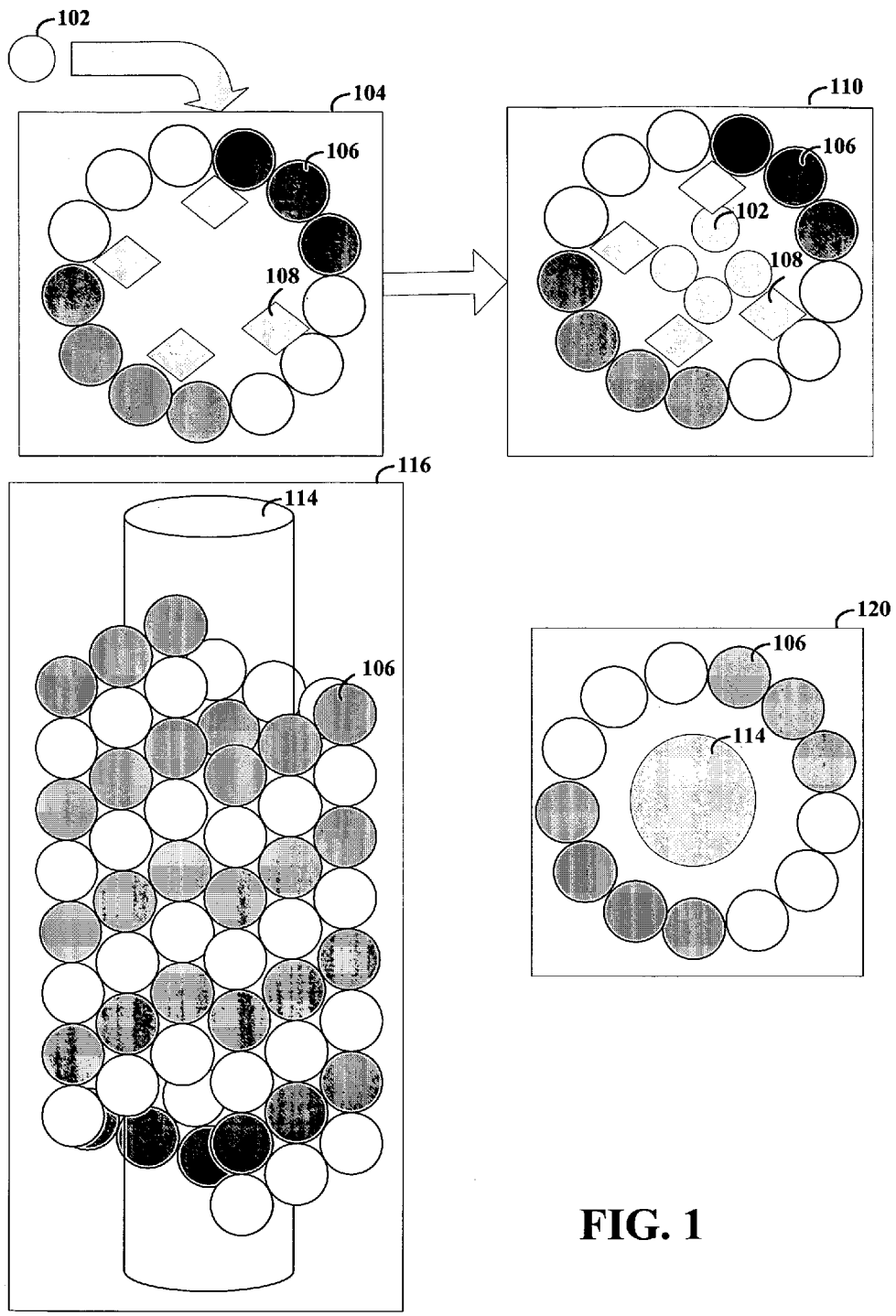
FIG. 1 depicts a nanowire device in different stages of construction, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention.

DETAILED DESCRIPTION

The present invention may be applicable to a variety of different types of devices and processes, and the invention has been found to be particularly suited for nano-scale metallic wire casting applications. While the present invention is not necessarily limited to such applications, various aspects of the invention may be appreciated through a discussion of various examples using this context.

According to an example embodiment of the present invention, a microtubule lumen casting approach is implemented for creating nanowires. The microtubule is used in accordance with the present invention to form metallic nanowires, which are cast by utilizing the hollow lumen of the microtubule.

Cell biology and nano-scale science share common goals of understanding and manipulating structures at the molecular level. In one embodiment, naturally occurring proteins are used to help guide the assembly of inorganic materials for building nano structures. In some implementations, proteins of the cellular cytoskeleton exhibiting linear modularity and reversible self-assembly, such as tubulin, are used in accordance with the present invention to form nanowires. The nanowires are cast by utilizing the hollow lumen of a microtubule, which is a dynamic cytoskeletal polymer made up of a hollow cylinder of α- and β-tubulin heterodimer subunits. Microtubules are selectively polymerized and stabilized by the anti-cancer drug paclitaxel. The interior wall of the microtubule is used for paclitaxel binding and also is the site for tubulin acetylation conferring microtubule stability.

A biological function for the hollow microtubule lumen was postulated to serve as a conduit for the transport of material. Kinetics studies have shown the ability for paclitaxel and for other molecules to diffuse inside microtubules. With these biological and physical features of microtubules in mind, one embodiment of the present invention enhances the functionality of the microtubule lumen by using it to shape metallic material.

One approach to creating nanowires, in accordance with the present invention, uses tubulin protein, polymerized into microtubules using paclitaxel. Silver ions are diffused into the lumen of the microtubule, with a subsequent reduction of the silver ions into silver solid using citric acid. The microtubule protein templates may then be destroyed with proteinase k digestion and with heat.

FIG. 1 depicts a nanowire device at different stages of construction, according to an example embodiment of the present invention. FIG. 1 includes a first stage 104, a second stage 110, a nanowire device 116 and a cross-sectional view of a nanowire device 120. To create a nanowire device, a person or device introduces the nanowire material 102 to a microtubule 106 at the first stage 104. The nanowire material 102 diffuses or otherwise enters the interior lumen of the microtubule 106 as depicted at the second stage 110. This process is used to form nanowire 114, which consists substantially of the material 102 and is surrounded by the microtubule 106 as shown in blocks 116 and 120.

Block 104 depicts microtubule 106 and molecule 108. Molecule 108 may be paclitaxel or another molecule that binds to the microtubule, such as the proteins, tau, katanin, acetylase and proteases. In one embodiment, molecule 108 is used during the synthesis of the microtubule. For example, paclitaxel has been shown to be useful in the synthesis of microtubules. In an alternate embodiment, molecule 108 is conjugated with nanowire material 102.

Nanowire material 102 is introduced to microtubule 106 and diffuses or otherwise enters the interior of microtubule 106. In an alternate embodiment where the nanowire material is conjugated with molecule 108, molecule 108 binds to the interior of the microtubule, thereby bringing nanowire material 102 into the interior of the microtubule. The second stage 110 depicts the nanowire material 102 within the microtubule 106. In one embodiment, the nanowire material enters the microtubule as part of a solution. For instance, the nanowire material can be a metal that enters the microtubule as a metal ion solution.

The nanomaterial 102 within the microtubule is solidified to form nanowire 114 as depicted in block 116 and the corresponding cross-sectional view of block 120. In one embodiment, the nanomaterial is solidified by reducing the metal ion solution using, for example, a redox reaction. The resulting nanowire 114 may be a continuous wire running the length of the microtubule or it may be multiple nanowires consisting of separate pieces of nanomaterial 102.

Figure 2:
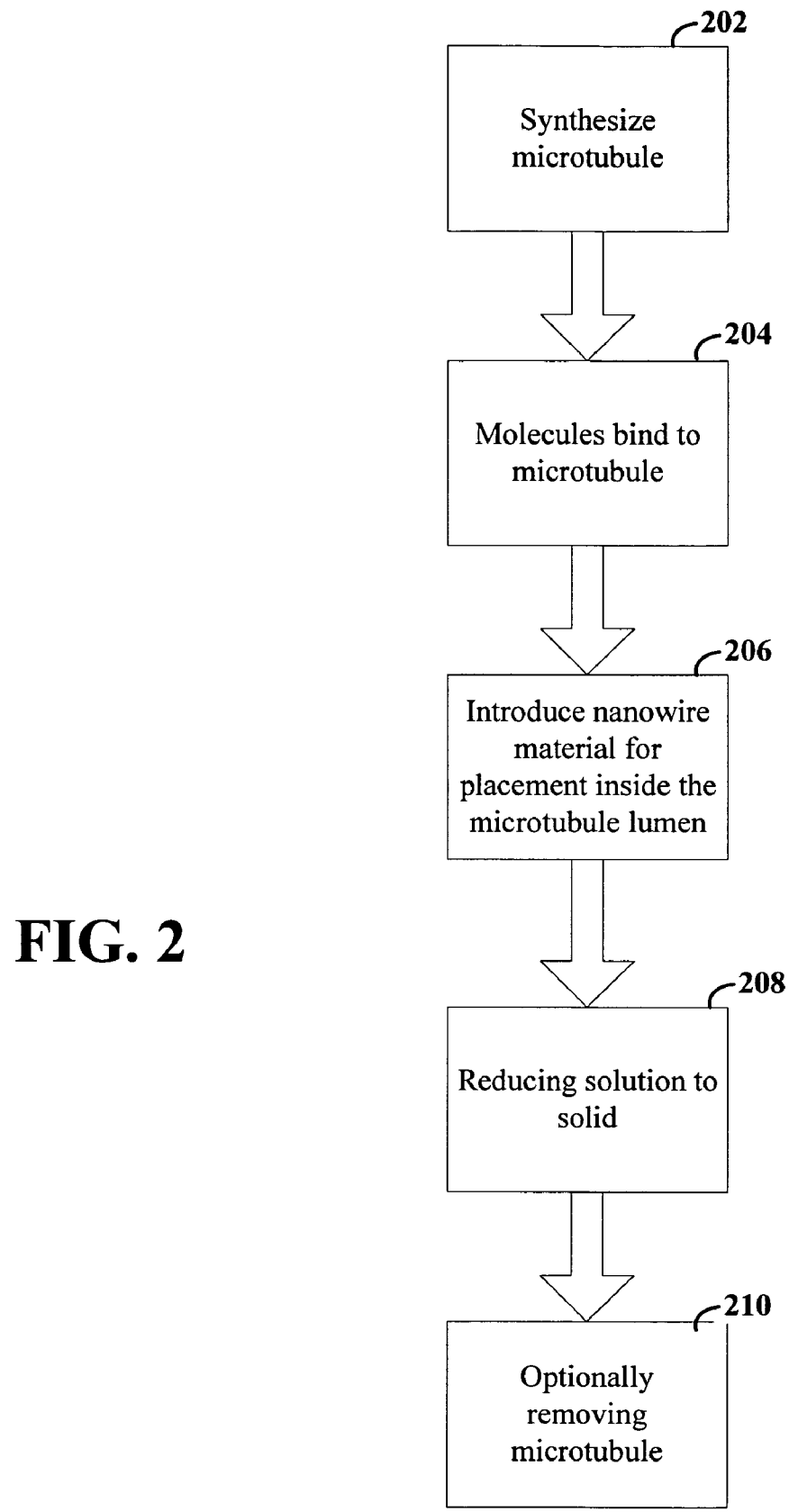
FIG. 2 depicts a flow chart for a method of constructing nanowires, according to an example embodiment of the present invention.

FIG. 2 depicts a flow chart for a method of constructing nanowires, according to another example embodiment of the present invention. The method may be implemented by an individual, an automated system or combination thereof. The flow chart begins with the synthesis of microtubules (block 202) and completes with either the reduction of the solution to a solid (block 208) or the optional removal of the microtubules from the nanowire (block 210).

The user of the method synthesizes the microtubules by polymerizing tubulin protein using one of several techniques. Using one such technique, another molecule, such as paclitaxel, is used to assist the polymerization. The nanowire material is then introduced and diffuses or otherwise enters the interior of the microtubule lumen as shown by block 206.

Using an alternate technique, a molecule that binds to the interior of the microtubule lumen can be introduced either during or after the polymerization process of 202 as depicted at block 204. In some instances, two molecules that each bind to a different one of the α- and β-tubulin heterodimer subunits are introduced to the microtubule lumen. The different molecules can also be selected to conjugate with different nanowire materials and the conjugated materials can be introduced as depicted by block 206. In this manner, the nanowire can be constructed using alternating material along the length of the nanowire.

The user next alters the state of the nanowire material as depicted at block 208. For instance, where the user introduces the nanowire material as a solution (block 206), the user alters the state of the nanowire material from a solution to a solid. The method of alteration varies depending upon the material. Using one such method of alteration, the user uses chemical reduction to change nanowire material ions from a solution to a solid.

The result of steps 202-208 is a nanowire substantially composed of the introduced nanowire material and surrounded by a microtubule. This structure is useful for a variety of applications, some of which are discussed herein; however, in some situations the user may desire that the microtubule be removed from the nanowire. To accomplish this, the user may optionally remove the microtubule as depicted by block 210. This can be accomplished by, for example, the application of heat, chemicals or combinations thereof.

In one embodiment of the present invention, nanowires having widths of less than 10 nanometers and lengths on the order of microns are created. Since some microtubules have an outer diameter of approximately 25 nanometers, the dimensions of these nanowires are consistent with the approximately 16 nanometers diameter interior of some known microtubule lumens (e.g., microtubule lumens made from bovine brain tubulin). This approach forms nanowires by filling up a naturally hollow protein polymer and allowing the inside dimensions to place a limit on the size of the resulting product.

In one embodiment of a method of forming nanowires using microtubule lumens, purified bovine brain tubulin in G-PEM buffer (80 mM PIPES, pH 6.8, 1 mM $MgCl_2$, 1 mM ethylene glycol tetra acetic acid (EGTA), 1 mM guanosine triphosphate) plus 10% glycerol is aliquoted and stored at −80 degrees Centigrade. Paclitaxel is dissolved in dimethylsulfoxide (DMSO), and stored at −20 degrees Centigrade. Silver nitrate and citric acid are each dissolved in double distilled water and stored at room temperature. Proteinase k is stored at −20 degrees Centigrade. All reactions may be carried out in double distilled water and protected from light.

0.1 mg/mL tubulin is polymerized in the presence of 4.55 uM paclitaxel for 40 minutes at 37 degrees Centigrade, followed by incubation in 73.58 mM silver nitrate for 43 minutes at 37 degrees Centigrade. The silver ions are then reduced to silver solid in 73.23 mM citric acid for 40 minutes at 37 degrees Centigrade. Samples are digested in 0.176 mg/mL proteinase k overnight for about 17 hours at 37 degrees Centigrade. A final 97 degrees Centigrade heating step for 30 minutes is then administered to the samples. Proteinase k digestion and heating are administered to destroy the microtubules, if desired.

Nanowires created using the above process may be visualized using transmission electron microscopy (TEM) visualization. TEM may be performed, for example, with a Philips CM12 TEM system operating at 80 kV. The TEM images can be produced by applying each sample to a 300 mesh nickel grid, allowed to dry for 5 minutes, and imaged directly with no fixation and no stains.

In accordance with one embodiment of the present invention, the microtubule protein is made by living cells; and can be mass-produced without the need for manual organic synthesis. Moreover, since the microtubule is a natural protein, it may be biologically compatible with living systems. The microtubules self-assemble efficiently and consistently into long filamentous structures with known dimensions, for example, having a 25 nanometer outside diameter and a 16 nanometer inside dimension, with lengths on the order of microns. The dimensions of the nanowire may thus be controlled by the dimensions of this microtubule template.

In another example, distinct ends of the microtubule, (i.e., a "plus end" and a "minus end") each having a distinct set of chemistry, structure, and biological properties, are used to organize the microtubules and their encased nanowires into defined arrangements. In this manner, the surface of the microtubule is left exposed and protein to protein interactions of microtubule-associated proteins (MAPs) and other molecules which bind to the outside surface still occur. For example, microtubule binding proteins are used to facilitate microtubule polymerization, control stability, and guide attachment and arrangement of the nanowires.

In another embodiment, motor proteins that bind to the outsides of microtubules may be used to exert force on the microtubule and nanowire to cause motion. Thus, the motor proteins are used to transport the microtubules along with the microtubules internal cargo of one or more nanowires.

In another example, the microtubule is still an integral component of a living cell's cytoskeleton. Alterations can be made in the tubulin amino acid sequence to diversify the structure of the microtubule and create a diversity of nanowires because tubulin consists of protein encoded at the DNA level. Accordingly, the nanowire cast from the inside lumen in accordance with the one embodiment of present invention is used to fill the microtubule lumen with various materials and to perform chemical reactions within.

Many medically-important pharmacological agents work by interacting with the microtubule. A combination of this drug information with nanowire technology in accordance with the present invention may provide a new interface for materials in medicine. For related information regarding controlled release of pharmacological agents, reference may be made, for example, to U.S. Pat. No. 5,492,696, U.S. Pat. No. 5,651,976, U.S. Pat. No. 5,705,191, and U.S. Pat. No. 6,280,759; each of these references is fully incorporated herein by reference.

In accordance with other embodiments of the present invention, different kinds of objects are placed inside the microtubule lumen, and different materials can be cast into different kinds of nanowires inside the microtubule lumen. In one such example embodiment, microtubules are made of a polymer of alpha- and beta-tubulin proteins. Different kinds of materials may be linked to alpha- or beta-tubulin, to give a regularly repeating wire of two alternating materials.

In another example embodiment, a molecule that binds inside the lumen of microtubules, such as paclitaxel, may be used to bring material inside. For example, the material may be connected to the paclitaxel, and be escorted into the lumen by the paclitaxel as the paclitaxel binds to the interior of the microtubule lumen. Proteins that bind to the inside of the lumen, such as tau, katanin, acetylase, and proteases, may be conjugated to the material, so as to bring the material into the inside of the lumen.

Since the nanowire is on the inside of the microtubule in accordance with an embodiment of the present invention, the outer microtubule surface may be used for microtubule-associated molecules that bind to the outside. A biosensor is used to detect molecular binding events on the surface of the microtubule, which may change the electrical conductivity of the nanowire inside, for example. One such biosensor is used to detect voltage changes due to changes in electrical conductivity of the nanowire.

And as a further embodiment, electrical and or magnetic signals within the nanowire are used to control the binding of molecules to or the release of molecules from, the microtubule. In one such example, an electrical current is applied to the nanowire to effect the release of molecules from the microtubule. The electrical current is then removed to allow for the rebinding of molecules.

In other embodiments, a material binding site is created that allows the placement of the binding site to either face the inside towards the microtubule lumen or face the outside on the microtubule exterior wall. For example, amino acid residue sequences which have affinities for different portions of the microtubule are created. The portion of the microtubule is selected base upon the crystal structure of the alpha- and beta-tubulin proteins of the microtubule. The amino acid sequences are incorporated into the proteins, and serve to direct the binding of nanowire materials to the proper locations. In this fashion nanowire material is then bound to the binding sites. For example, a coaxial nanowire structure (i.e., an inner nanowire contained within a hollow outer nanowire) may be produced in this way. In another such embodiment, different materials may be linked to the alpha- and beta-tubulin at these material binding sites. Nanowires produced in this way will consist of a periodicity of regularly-alternating materials that correspond to the periodicity of alternating alpha- and beta-tubulin of the microtubule. Many variations of this inside- and outside-combination of materials may be used to generate diversity in nanowires.

In another example embodiment, if the metal cast inside a microtubule in accordance with the present invention is magnetic, a magnetic field may be used to control the direction and movement of the metal and the microtubule together. For instance, the magnetic field is applied using an external magnetic source that attracts the metal portion of the nanowire. In another example, an electrical current is applied to the nanowire which generates a magnetic field which exerts a force on the nanowire.

Another implementation involves an array of microtubule binding molecules that guide the orientation, positioning, and connectivity of the microtubules and nanowires. For instance, specific proteins that bind the specific ends of a microtubule are used to guide each end of the microtubule to a different location.

In other embodiments, microtubules, housing metal inside, are placed into living cells and/or organisms. The microtubule, with metal inside, is integrated into the existing microtubule cytoskeleton within the cell. Magnetic sensing of the nanowire material is used to track the motion of individual protein complexes inside living cells. For example, a cell with magnetic material inside its microtubules creates a magnetic field or distribution pattern of metallic electronic signal, which is indicative of the position of the cell and the metallic nanowire material within the cell. Thus, the magnetic properties of such a cell facilitate tracking the motion of the cell and distinguishing the cell from other cells. Moreover, a cell whose microtubules are filled with a material can be controlled by external forces. For instance, external magnetic fields are applied to a microtubule filled with a magnetic material to cause movement of the cell and a change in cell shape in response to the magnetic field.

In another embodiment of manipulation of nanowires in accordance with embodiments of the present invention, the nanowire device is designed to rotate radially, either clockwise or counter-clockwise, within the microtubule. This mechanical gear type arrangement is analogous to a toilet paper's cardboard roll rotating about its holder rod. Alternatively, the nanowire is designed to allow movement longitudinal with respect to the microtubule and is used as a piston. Motor proteins are used to exert motion, either rotationally or longitudinally, on the microtubule and/or nanowire. For example, motor proteins, such as kinesin and dynein, have distinct directional movement towards the plus-end and minus-end of a microtubule, respectively. Such motor proteins immobilized on an external surface are used to transport microtubules with their nanowire cargo. In this manner, the microtubule is used to move about and carry material inside. Proteins, such as Dam1, can surround the microtubule with its nanowire and allow the nanowire to slide rotationally and longitudinally. This technique is used for directional positioning and to create a freedom of motion for the device.

While the present invention has been described with reference to several particular example embodiments, those skilled in the art will recognize that many changes may be made thereto without departing from the scope of the present invention.

What is claimed is:

1. A method for casting a nanowire, the method comprising:
   introducing a solution of a nanowire material to a microtubule; and
   using the microtubule and the nanowire material from the solution to form a nanowire having a shape defined by the microtubule.

2. The method of claim 1, further including forming the microtubule by polymerizing the microtubule using paclitaxel.

3. The method of claim 1, further including, prior to forming the nanowire, conjugating the nanowire material with a molecule that binds to a wall of the microtubule.

4. The method of claim 1, wherein introducing a solution of a nanowire material includes introducing a solution having first and second nanowire materials, further including
   conjugating the first nanowire material with a first molecule that binds to a first portion of a wall of the microtubule,
   conjugating the second nanowire material with a second molecule that binds to a second portion of a wall of the microtubule, and
   wherein using the nanowire material from the solution and the microtubule to form a nanowire forms a nanowire having both the first and second nanowire materials.

5. The method of claim 1, further including
   conjugating the first nanowire material with a first molecule that binds to a first portion of a wall of the microtubule,
   conjugating the second nanowire material with a second molecule that binds to a second portion of a wall of the microtubule, and
   wherein using the nanowire material from the solution and the microtubule to form a nanowire forms a coaxial nanowire structure having both the first and second nanowire materials.

6. The method of claim 1, wherein the nanowire material includes at least one of a metal and a semiconductor.

7. The method of claim 1, wherein using the microtubule and the nanowire material from the solution to form a nanowire includes reducing an ionized form of the nanowire material.

8. The method of claim 1, further including removing the microtubule from the nanowire using at least one of heat and a chemical reaction.

9. The method of claim 1, wherein introducing a solution of a nanowire material includes introducing a solution having first and second nanowire materials, further including
   forming a first material binding site on a first portion of the microtubule,
   forming a second material binding site on a second portion of the microtubule,
   binding the first nanowire material to the first material binding site and the second nanowire material to the second material binding site, and
   wherein using the nanowire material from the solution and the microtubule to form a nanowire forms a nanowire having both the first and second nanowire materials.

10. The method of claim 1, wherein introducing a solution of a nanowire material includes introducing a solution having first and second nanowire materials, further including
    forming a first material binding site on a first portion of the microtubule,
    forming a second material binding site on a second portion of the microtubule,
    binding the first nanowire material to the first material binding site and the second nanowire material to the second material binding site, and
    wherein using the nanowire material from the solution and the microtubule to form a nanowire forms a coaxial nanowire structure having both the first and second nanowire materials.

11. The method of claim 1, further including monitoring changes in the electrical properties of the nanowire due to molecules interacting with the microtubule.

12. The method of claim 1, further including moving the nanowire by controlling the movement of the microtubule using proteins.

13. The method of claim 1, further including
    inserting the microtubule and the nanowire into a biological cell, and
    controlling the physiology of the biological cell from an external source using electrical or magnetic signals exerted on the nanowire.

14. The method of claim 1, further including moving the nanowire longitudinally within the microtubule.

15. The method of claim 1, further including
using the characteristics of a plus end of the microtubule to position the plus end of the microtubule relative to a first location, and
using the characteristics of a minus end of the microtubule to position the minus end relative to a second location.

16. The method of claim 1, further including using microtubule binding molecules to guide the microtubule and the nanowire.

17. The method of claim 1, further including using electrical or magnetic signals to guide the orientation, positioning, and connectivity of the microtubule and the nanowire.

18. The method of claim 1, further including
inserting the microtubule and the nanowire into a biological cell, and
determining the location and properties of the biological cell by detecting the nanowire using an electrical or magnetic signal.

19. The method of claim 1, further including
inserting the microtubule and the nanowire into a biological cell, and
controlling physiology of the biological cell from an external source using electrical and magnetic signals exerted on the nanowire.

20. A method for forming a nanowire, the method comprising:
aliquoting and storing tubulin in G-PEM buffer plus glycerol;
polymerizing tubulin in the presence of paclitaxel solution to produce a microtubule having a lumen;
incubating the microtubule in a silver nitrate solution;
reducing silver from the silver nitrate solution to silver solid in citric acid, thereby forming a nanowire; and
wherein a substantial portion of the silver solid is within the microtubule lumen.

21. The method of claim 20, wherein the tubulin consists of bovine brain tubulin.

22. The method of claim 20, wherein:
the silver nitrate solution is produced by dissolving silver nitrate in double distilled water, and
the paclitaxel solution is produced by dissolving and storing paclitaxel in dimethylsulfoxide at about −20 degrees Centigrade.

23. The method of claim 20, further including stripping the microtubule from the nanowire using proteinase k digestion and heating to about 97 degrees Centigrade for about 30 minutes.

24. The method of claim 20, further including using motor proteins to move the microtubule and the nanowire.

25. The method of claim 20, further including
using the characteristics of a plus end of the microtubule to position the plus end of the microtubule relative to a first location, and
using the characteristics of a minus end of the microtubule to position the minus end relative to a second location.

26. The method of claim 20, further including
inserting the microtubule and the nanowire into a biological cell, and
determining the location of the biological cell by detecting the nanowire using an electrical sensor.

* * * * *